United States Patent
Maher et al.

(10) Patent No.: US 8,557,270 B2
(45) Date of Patent: Oct. 15, 2013

(54) INTERCONNECTED POROUS NON-DEGRADABLE POLY(VINYL) ALCOHOL IMPLANT AND METHOD OF MANUFACTURE

(75) Inventors: Suzanne A. Maher, Highland Lakes, NJ (US); Kenneth Ng, New York, NY (US); Tony Chen, New York, NY (US); Florian Wanivenhaus, Vienna (AT)

(73) Assignee: New York Society for the Ruptured and Crippled Maintaining the Hospital for Special Surgery, New York, NY (US)

(*) Notice: Subject to any disclaimer, the term of this patent is extended or adjusted under 35 U.S.C. 154(b) by 90 days.

(21) Appl. No.: 13/349,365

(22) Filed: Jan. 12, 2012

(65) Prior Publication Data
US 2012/0178836 A1 Jul. 12, 2012

Related U.S. Application Data

(60) Provisional application No. 61/432,098, filed on Jan. 12, 2011.

(51) Int. Cl.
*C08J 9/26* (2006.01)

(52) U.S. Cl.
USPC ............... 424/422; 424/423; 521/61; 521/63; 521/141

(58) Field of Classification Search
USPC ....................... 521/61, 63, 141; 424/422, 423
See application file for complete search history.

(56) References Cited

U.S. PATENT DOCUMENTS

| | | | |
|---|---|---|---|
| 5,981,826 A | 11/1999 | Ku et al. | |
| 7,972,628 B2 * | 7/2011 | Ratner et al. | 424/499 |
| 2008/0154372 A1 | 6/2008 | Peckham | |
| 2009/0017096 A1 | 1/2009 | Lowman et al. | |

OTHER PUBLICATIONS

Masaya Yamamoto et al. Promotion of fibrovascular tissue ingrowth into porous sponges by basic fibroblast growth factor. Journal of Materials Science: Materials in Medicine, 2000, vol. 11, p. 213-218, especially, p. 213-214, 216.
Qingliang Zhou et al. Microstructure and Mechanical Properties of Poly(L-lactide) Scaffolds Fabricated by Gelatin Particle Leaching Model, Journal of Applied Polymer Science, 2005, vol. 98, pp. 1373-1379.
Abusafieh et al. (1997) Development of Self-Anchoring Bone Implants. I. Processing and Material Characterization, *J Biomed Mater Res.* 38(4):314.
Bichara et al. (2010) Porous Poly(vinyl alcohol)-Alginate Gel Hybrid Construct for Neocartilage Formation using Human Nasoseptal Cells, *J. Surg. Res.* 163:331.
Bos et al. (2002) Specific Enzymatic Treatment of Bovine and Human Articular Cartilage: Implications for Integrative Cartilage Repair, Arthritis Rheum. 46(4): 976.
Bodugoz-Senturk et al. (2009) Poly(vinyl alcohol)-acrylamide Hydrogels as Load-Bearing Cartilage Substitute, *Biomaterials* 30(4):589.
Bodugoz-Senturk et al. (2008) The Effect of Polyethylene glycol of the Stability of Pores in Polyvinyl Alcohol Hydrogels during Annealing, *Biomaterials* 29(2):141.
Brittberg et al. (2003) Articular Cartilage Engineering with Autologous Chrondrocyte Transplantation: A Review of Recent Developments, *J. Bone Joint Surg Am* 85(Supp3): 109.
Buckwalter et al. (1998) Articular Cartilage: Degeneration and Osteoarthritis, Repair, Regeneration, and Transplantation, *Instr. Course Lect.* 47:487.
Cho et al. (2005) Fabrication and Characterization of Porous Alginate/ Polyvinyl Alcohol Hybrid Scaffolds for 3D Cell Culture, *J. Biomater. Sci. Polm. Ed.* 16(8):933.
Dai et al. (2000) Gel Impregnated Pore Membrane with Mesh-size Asymmetry for Biohybrid Artificial Organs, *Biomaterials* 21(13):1363.
Freedman et al. (2003) Marrow Stimulation Technique to Augment Meniscus Repair, *Arthroscopy* 19:794.
Fussell et al. (2005) The Effect of Protein-free versus Protein-containing Medium on the Mechanical Properties and Uptake of Ions of PVA/PVP Hydrogels, *J. Biomater. Sci. Polm. Ed* 16(4):489.
Gross et al. (2003) Cartilage Resurfacing: Filling Defects, J. *Arthroplasty* 18 (3 Suppl.1):14.
Jurvelin et al. (1997) Optical and Mechanical Determination of Poisson's ratio of Adult Bovine Humeral Articular Cartilage, *J. Biomech.* 30(3): 235.
Maher et al. (2007) Nondegradable Hydrogels for the Treatment of Focal Cartilage Defects, *J Biomed Mater Res* 83(A):145.
Mow et al. (1993) Biomechanics of Diarthrodial Joints: A Review of Twenty Years of Progress, J. *Biomech. Eng.* 115:460.
Mow et al. (1980) Biphasic Creep and Stress Relaxation of Articular Cartilage in Compression: Theory and Experiments, *J Biomech. Eng*, 102(1): 73.
Noguchi et al. (1991) Poly(vinyl alcohol) Hydrogel as an Artificial Articular Cartilage: Evaluation of Biocompatibility, *J. Applied Biomater.* 2:101.
Oka et al. (1990) Development of an Artificial Articular Cartilage, *Clin. Mater.* 6:361.
Scholten et al. (2011) A Semi-degradable Composite Scaffold for Articular Cartilage Defects, *J. Biomedical Materials Res.* A 97(A):8.
Stammen et al., (2001) Mechanical Properties of a Novel PVA Hydrogel in Shear and Unconfined Compression, *Biomaterials* 22(8):799.

(Continued)

*Primary Examiner* — Irina S Zemel
(74) *Attorney, Agent, or Firm* — Leason Ellis LLP

(57) ABSTRACT

The present invention relates to a method of manufacture of an interconnected porous non-biodegradable polymer implant suitable for implantation into a mammal for the treatment, repair or replacement of defects or injury in musculoskeletal tissue, wherein the mechanical properties of the implant can be controlled by varying the concentration of the non-biodegradable polymer and/or varying the duration and number of freeze-thaw cycles and the interconnected porous non-biodegradable polymer implant has sufficient percent porosity and pore diameter to facilitate integration of cells and attachment within the mammal via ingrowth of surrounding tissue. The present invention also relates to an implant manufactured by the method.

19 Claims, 8 Drawing Sheets

(56) References Cited

OTHER PUBLICATIONS

Swieszkowski et al. (2006) An Elastic Material for Cartilage Replacement in an Arthritic Shoulder Joint, *Biomaterials* 27(8):1534.

Szerb et al. (2005) Mosaicplasty: Long-term Follow-up, *Bull Hosp. Jt. Dis.* 63:54.

Thomas et al. (2004) The Effect of Dehydration History on PVA/PVP Hydrogels for Nucleus Pulposus Replacement, *J. Biomed. Mater. Res. B Appl. Biomater.* 69(2):135.

van de Breevaart Bravenboer et al. (2004) Improved Cartilage Integration and Interfacial Strength after Enzymatic Treatment in a Cartilage Transplantation Model, *Arthritis Res. Ther.* 6(5): R469.

* cited by examiner

INTERCONNECTED POROUS NON-DEGRADABLE POLY(VINYL) ALCOHOL IMPLANT AND METHOD OF MANUFACTURE

CROSS REFERENCE TO RELATED APPLICATION

The present application claims priority to U.S. patent application Ser. No. 61/432,098, filed Jan. 12, 2011, which is hereby incorporated by reference in its entirety.

FIELD OF INVENTION

The present invention is in the field of manufacturing porous non-degradable poly(vinyl) alcohol implants suitable for implantation into a mammal, to treat, repair or replace defects and/or injury to musculoskeletal tissue.

BACKGROUND OF THE INVENTION

Articular cartilage is a hydrated and lubricated joint tissue that allows for the relative movement of opposing joint surfaces under high loads (Scholten et al. (2011): Buckwalter et al. (1998); Mow et al. (1993)). Mature articular cartilage does not possess an intrinsic ability to heal, since it is avascular and lacks a source of mesenchymal cells (Scholten et al. (2010); Buckwalter et al. (1998)).

Current operative procedures for the treatment of articular cartilage damage generally fall into four categories: 1. non-transplant salvage operations such as abrasion arthroplasty; 2. mosaicplasty in which a cartilage-bone plug is transplanted into a joint which is minimally weight bearing; 3. reimplantation of autogenously isolated and expanded cells; and 4. the implantation of allografts (Maher et al. (2007); Szerb et al. (2005); Freedman et al. (2003); Brittburg et al. (2003); Gross (2003)). However, all of these techniques have their limitations, and do not prevent the progression of the osteoarthritis, which often propagates from the focal defect. Furthermore, over 33% of those affected by arthritis are under age 65. Accordingly, the number of young patients with total knee replacement, the end stage treatment for arthritis, is increasing. Performance of joint replacements in younger patient populations is less satisfactory than for older patients, oftentimes leading to multiple revision surgeries, each with successively diminishing longevity.

One proposed method for an alternative treatment is the use of a non-degradable synthetic non-cell derived implant to stabilize a chondral defect, thereby protecting adjacent tissue from degradation. Ideally, the scaffold would carry and distribute load similarly to native tissue, and also provide a mechanism for long-term fixation (Scholten et al. (2011)). While non-degradable hydrogel scaffolds (hydrophilic, crosslinked, hydrated polymeric networks), such as those made from poly(vinyl) alcohol (PVA), have shown to be promising in in vivo animal studies (Noguchi et al. (1991); Oka et al. (1990)), many have failed due to the lack of a porous periphery which would be required to facilitate cell migration and integration (Maher et al. (2007); Swieszkowski et al. (2006); Stammen et al. (2001)). Additionally, the mechanical properties of the scaffolds developed thus far are unable to carry joint loads of native tissue at the time of implantation (Maher et al. (2007)).

Moreover, the techniques developed thus far for creating porous PVA scaffolds either do not enable control over the mechanical properties of the end-product or do not enable the formation of a truly interconnected porous network. For example, one technique created a hybrid cellulose-PVA scaffold, intended to enable ultra-filtration and dialysis for bio-hybrid artificial organs. However, this method of manufacture did not enable control over the mechanical properties, nor control over porosity (Dai et al. (2000)). Previous studies have utilized PVA mixed with other compounds to form a porous PVA construct. One technique mixed polyethylene glycol (PEG) with polyvinyl alcohol. The binary solution was designed such that the PEG does not gel with freeze-thawing of the PVA and is responsible for the resulting porous network. PEG is then washed out and replaced with water (Bodugoz-Senturk et al. 2008). Another technique involved mixing polyacryl amide with polyvinyl alcohol (Bodugoz-Senturk et al. 2009). The solution is then gelled in order to structurally reinforce the porous network formed within the PVA. These porous PVA constructs have been shown to support cellular activity (Bichara et al.), but the pores only appear to be partially interconnected, with many pores appearing to be bubbles of fluid. Moreover, control over the mechanical properties and the porosity is not possible using the aforementioned techniques.

Therefore, there is a need in the art for a more reliable method to treat patients with chondral defects, especially young active ones, early in the course of the problem, thus delaying or eliminating the need for total joint replacement, and a real need in the art for a process for manufacturing PVA scaffolds where there is precise control over the mechanical properties and porosity of the resulting scaffold.

SUMMARY OF THE INVENTION

The present invention overcomes the problems in the art by providing a method that allows for precise control over the morphology of the interconnected porous network and the mechanical properties of an interconnected porous non-degradable polymer implant during manufacture. The resulting interconnected porous non-biodegradable polymer implant is suitable for implantation into a mammal, to treat, repair or replace defects and/or injury to musculoskeletal tissue including bone, tendon, ligaments, cartilage and the discs of the spine. In a preferred embodiment the implant is used to stabilize a chrondral defect, which is a defect in the articular cartilage at the end of the bones. In a most preferred embodiment, the chondral defect is found in the knee. The implant would not only repair the defect but protect the surrounding tissue from degradation.

Specifically, the method of the current invention allows for the control of the mechanical properties by varying the percent of non-biodegradable polymer and/or the duration and number of freeze-thaw cycles.

The method of manufacture of the construct, implant or scaffold includes the following steps:

Soaking a sponge containing a biodegradable polymer under vacuum in deionized water for a period ranging from 1 hour to 5 days;

Centrifuging the construct during the soaking process to remove trapped air bubbles;

Substituting a non-biodegradable polymer into the sponge under gentle agitation in steps of increasing concentration up to the desired concentration;

Freezing the construct to about −20° C. for about 4 to 24 hours and then thawing the construct at about 25° C. for about 4 to 12 hours, wherein the freeze-thaw process is performed 1-8 times;

Enzymatically digesting away the biodegradable polymer in the sponge; and

Optionally further digesting the non-biodegradable polymer to obtain a scaffold with larger pore sizes.

The resulting implant, construct or scaffold is of sufficient percent porosity and pore diameter to facilitate integration of cells and attachment within the mammal via ingrowth of surrounding tissue, as well has being sufficiently strong to carry load similar to that of native tissue.

In one embodiment, the non-biodegradable polymer used in the implant, construct or scaffold is poly(vinyl) alcohol or PVA. It is preferred that the final concentration of the PVA in the scaffold is about 10% to 40%, with 40% being most preferred.

In a further embodiment, the biodegradable polymer contained in the sponge is collagen, gelatin, poly(lactic) acid, poly(glycolic) acid, or alginate.

In one embodiment, the freezing of the sponge takes place at about −20° C. for about 20 hours and thawing the sponge takes place at about 25° C. for about 4 hours and the freeze-thaw process is performed 6 times.

In a further embodiment, the porosity of the implant can be controlled by varying the morphology of the starting material sponge, specifically the porosity and wall thickness of the sponge.

The preferred enzyme for digesting the biodegradable polymer in the sponge is collagenase, and it is preferred that the digestion take place for 24 hours. However, the mechanical properties of the implant or scaffold can also be controlled by varying the degree of enzymatic digestion of the biodegradable polymer and of the non-biodegradable polymer. The collagen or gelatin scaffold can be left undigested to facilitate the attachment of the cells.

In a further embodiment, the PVA scaffold is fully dehydrated, air dried, then placed in hydrochloric acid and finally washed with deionized water to create pores larger than that created with collagen/gelatin scaffold alone.

A further embodiment of the present invention is an interconnected porous non-biodegradable polymer implant, construct or scaffold suitable for implantation into a mammal, in need thereof to treat, replace or repair defects or injury in musculoskeletal tissue, manufactured by the method set forth above.

In one embodiment, the interconnected porous non-biodegradable polymer implant has an average pore size of greater than 10 μm.

In one embodiment, the interconnected porous non-biodegradable polymer implant has an average pore size of greater than 30 μm.

In one embodiment, the interconnected porous non-biodegradable polymer implant has an average pore size of greater than 100 μm.

The properties of the implant, construct or scaffold can be varied by varying the manufacturing conditions. In particular, the present porosity and pore diameter can be made to vary regionally throughout the implant, with a preferred embodiment being a scaffold with zero porosity at the center in order to facilitate an ability to carry load, and a pre-determined porosity at the periphery, in order to optimize the ability of the implant to integrate with biological tissue. The pore size required to facilitate cell migration depends on the tissue with which integration is required and the target cells within. The modulus of the porous periphery can be tailored to optimize the response of cells. An implant with these properties can be made by coring a section from the center of the implant after performing the first four steps but prior to enzymatic digestion, and adding additional non-biodegradable polymer to this section of the sponge, performing additional freeze-thaw cycles, and enzymatically digesting the construct.

The implant, construct or scaffold of the present invention can be used to treat, replace or repair defects or injury in any musculoskeletal tissue, including cartilage, bone, tendon, ligaments, and the discs of the spine.

Moreover, the implants of the present invention are suitable for implantation into mammals, more specifically humans.

BRIEF DESCRIPTION OF THE DRAWINGS

For the purpose of illustrating the invention, there are depicted in drawings certain embodiments of the invention. However, the invention is not limited to the precise arrangements and instrumentalities of the embodiments depicted in the drawings.

DETAILED DESCRIPTION OF THE INVENTION

Figure 1:
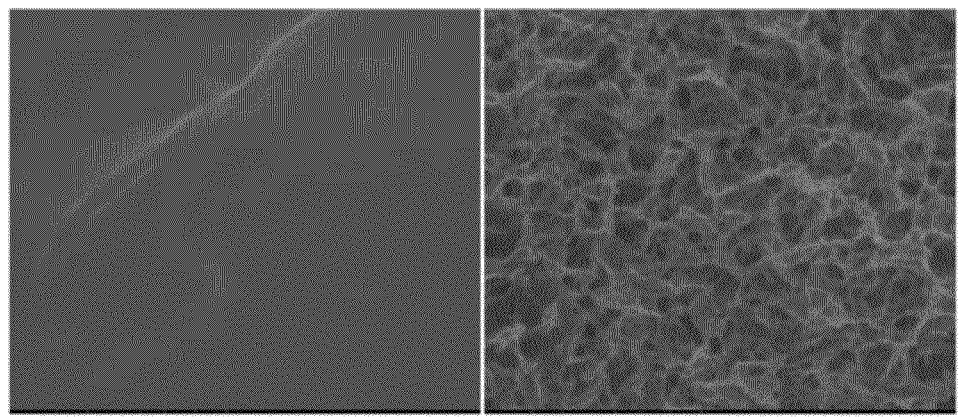
FIG. 1 depicts an environmental scanning electron microscopy ("ESEM") image of non-porous and porous PVA gels. The porous gel depicted on the right was manufactured by the method of the present invention.

The present invention is a novel method for manufacturing an implant, construct or scaffold made of a non-biodegradable polymer, preferably poly(vinyl) alcohol (PVA), that enables complete control over the mechanical properties of the implant as well as the morphology of the interconnected porous network.

The present invention also includes an implant, construct or scaffold made by the novel method. Such an implant, construct or scaffold is suitable to mimic native tissue and is suitable for implantation into a mammal, preferably a human, in order to treat, repair or replace various musculoskeletal tissues and to treat cartilage or osteochondral defects.

DEFINITIONS

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

The terms "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

The terms "implant", "construct", and "scaffold" are used interchangeably throughout this application and means any material inserted or grafted into the body that maintains support and tissue contour.

The term "porous" as used in the application means having pores, which are defined as a minute opening.

The term "interconnected" as used in the application means having internal connections between parts or elements.

The term "subject" as used in this application means an animal with an immune system such as avians and mammals. Mammals include canines, felines, rodents, bovine, equines, porcines, ovines, and primates. Avians include, but are not limited to, fowls, songbirds, and raptors. Thus, the invention can be used in veterinary medicine, e.g., to treat companion animals, farm animals, laboratory animals in zoological parks, and animals in the wild. The invention is particularly desirable for human medical applications The term "in need thereof" would be a subject known or suspected of having an injury to or defect in any musculoskeletal tissue including but not limited to cartilage, bone, tendon, ligaments, and the discs of the spine.

The terms "treat", "treatment", and the like refer to a means to slow down, relieve, ameliorate or alleviate at least one of the symptoms of the defect or injury or reverse the defect or injury after its onset.

A "chondral defect" is defined as a defect in the articular cartilage at the end of the bones.

The term "polymer" means a large molecule composed of repeating structural units often connected by covalent chemical bonds. Polymers can be natural or synthetic. "Biodegradable polymers" are those that can be degraded by living organisms or molecules produced by living organisms such as enzymes and other proteins, and "non-biodegradable polymers" cannot be degraded by such enzymes or proteins. The non-biodegradable polymer as used herein means any polymer which has mechanical properties that can be controlled separately by varying the polymer concentration and/or the method of polymerization such as freeze-thawing.

The present invention is a method of manufacture which results in a porous PVA scaffold, where a given porosity and the mechanical properties can be controlled. This will allow the independent tailoring of the morphology so as to optimize the ability of cells to migrate into the scaffold, while also controlling the mechanical properties to optimize the response of the inward migrating cells such that their ability to lay down matrix (hence integrate with the host tissue) is maximized. Thus, the method of manufacture has been designed to:

1. Allow for precise control of mechanical properties without changing the functional porosity of the scaffold through a combined approach of controlling PVA concentration and/or freeze-thaw cycles; and controlling the functional porosity which is controlled independently of the PVA solution.
2. Allow for precise control of the morphology of the interconnected porous network through use of a collagen mesh. PVA is infused into the mesh, solidified, and the mesh is then digested away.
3. Allow for precise control of the morphology of the interconnected porous network through controlled digestion of the PVA using hydrochloric acid.
4. Allow for the method of manufacture to be altered to facilitate a regional variation in construct porosity, thereby allowing for a central load carrying core, which is augmented with a porous periphery for cell infiltration.
5. Allow for control over the depth of penetration of host cells into the scaffold by controlling the degree of collagen digestion prior to use.
6. Allow for control over the reaction of the cells by controlling the mechanical properties (modulus) of the porous scaffold into which they migrate.

Method of Manufacture of the PVA Implant, Construct or Scaffold

The method of the present invention includes at least the following steps:

1. Hydration of a sponge made of or containing a biodegradable polymer;
2. Replacement of water with non-biodegradable polymer solutions;
3. Cross-linking the non-biodegradable polymer, by techniques known in the art, such as freeze-thawing of the construct;
4. Removal of the biodegradable polymer from the sponge to form macroporous network; and
5. Optional digestion of the non-biodegradable polymer using hydrochloric acid.

Hydration of Sponges Made of or Containing a Biodegradable Polymer

Gelatin sponges, which are the preferred starting material, are sterile absorbable gelatin products used to control bleeding. They are available commercially from Ethicon-Johnson & Johnson, Pfizer, Baxter, and Medtronic. The sponge can also be made of or contain other biodegradable polymers including, but not limited to, collagen, poly(lactic acid), poly (glycolic acid) and alginate.

Moreover the sponge's size, porosity and wall thickness can be varied depending on the needs of the final implant. The porosity of the starting or initial sponge determines the porosity, however, the porosity of the final implant can also be varied and controlled by a controlled digestion with hydrochloric acid.

The sponge is hydrated by soaking it in deionized water for 1 hour to 5 days. While the preferred method is soaking the sponge under vacuum cycled on and off for 6 hours for 1 day, a person of skill in the art would easily be able to determine a sufficient amount of time wherein the sponge is saturated with water.

The sponge is then centrifuged to remove the trapped air bubbles. The preferred method is at 3000 g for 1 hour at a time, 3-5 times, with gentle agitation between the centrifugations to restore the original shape. However, a person of skill could easily determine the extent of centrifugation necessary to remove air bubbles from the sponge. Another technique is the intermittent application of a vacuum for 30 minutes on and 30 minutes off, with agitation between the vacuum steps, for 3-5 times.

Replacement of the Water with Non-Biodegradable Polymer

The next step in the method of the invention is replacement of the water in the sponge with poly(vinyl) alcohol or PVA. While PVA is preferred, any non-biodegradable polymer which has mechanical properties that can be controlled separately by varying the polymer concentration and/or the method of polymerization such as freeze-thawing can be used.

The mechanical properties of the final scaffold are determined by the final concentration of the PVA in the scaffold. Generally, the higher the final concentration of PVA in the scaffold, the stiffer the scaffold. A scaffold with a higher concentration of PVA can generally withstand a higher load.

The PVA is substituted into the sponge under gentle agitation in steps of increasing concentration up to the desired concentration. PVA solutions of varying concentration are made and the sponges soaked until the desired concentration is obtained. The PVA solutions range from 1% to 40% weight/volume solutions, up to the desired final concentration, with the preferred final concentration of PVA scaffolds ranging from 10% to 40%. The preferred final concentration will depend upon the final use of the scaffold, as determined by the person of skill. However, scaffolds with 40% PVA have the mechanical properties most similar to that of native tissue.

The preferred method for substituting the PVA for water is to sequentially soak the sponges in the series of PVA solutions for 5 days under gentle agitation and rocking. At the final desired concentration, an additional change of fresh PVA solution is performed prior to freezing and thawing. The exact time of soaking will depend upon the final desired concentration of the PVA in the scaffold, as determined by a person of skill in the art.

Freeze-Thaw of the Construct

The PVA scaffolds are then subject to a series of freeze-thaw cycles. PVA offers the advantage of being physically cross-linked using freeze-thaw cycles, without the need for use of potentially toxic cross-linking agents. During freezing, water freezes and cause regions of high PVA crosslinks to form. As the PVA chains come in close contact with one another, crystallite formation and hydrogen bonding can occur between the chains. These interactions remain intact following thawing, and thereby create a three-dimensional network. Thus, the mechanical properties of the scaffold can be controlled by increasing the number of freeze-thaw cycles such that the amount of hydrogen bonding and crystallite formation can be increased. The increase in freeze-thaw cycles increases the strength of the construct. The mechanical properties can also be controlled by the duration and rate of freezing and thawing.

The preferred method involves freezing the construct at about −20° C. for about 20 hours and then thawing the construct at about 25° C. for about 4 hours wherein the freeze-thaw process is repeated 5 additional times (6 total freeze-thaw cycles). However, this part of the process can be easily varied by the person of skill in order to vary the mechanical properties of the construct as desired. Both the number of hours of freezing and/or thawing can be varied as well as the number of cycles. For example, the total number of freeze-thaw cycles can range from 1 to 8, with 6 being the preferred number. The construct can be frozen at each interval for a time ranging from 4 to 24 hours, with 20 hours being preferred. The thaw time can range from 4 to 12 hours, with 4 hours being preferred.

While PVA is the preferred non-biodegradable polymer, and freeze-thawing the preferred method for cross-linking the PVA, other non-biodegradable polymers, and methods known in the art to cross-link such polymers, can be used.

Removal of the Biodegradable Polymer from the Sponge to Form Macroporous Network The next step of the method of the invention is removing the gelatin or other biodegradable polymer from the sponge so as to form a macroporous network. This is accomplished by incubating the sponges with an enzyme capable of digesting the biodegradable polymer from the sponge. The preferred enzyme is collagenase, but other enzymes suited to digest the polymer being used in the sponge will be apparent to those of skill in the art. The concentration of the enzyme ranges from 300 to 1000, with 500 enzyme activity units/milliliter being the preferred amount. The sponges are digested from 12 hours to 48 hours, with 24 hours being preferred.

It will also be understood that the method of manufacture can be altered to allow for control over the depth of penetration of host cells into the scaffold by controlling the degree of enzymatic digestion prior to use of the scaffold.

Digestion of Non-Biodegradable Polymer to Increase Pore Size Beyond that of the Starting Material Sponge In the event that a sponge made of or containing a biodegradable polymer is not available to create a final scaffold with sufficiently large pores for final use, the pores created can be increased in size uniformly through the following steps:

1. Dehydrate the scaffold through 70% ethanol for 30 minutes;
2. Further dehydrate with 100% ethanol for 30 minutes;
3. Air dry in hood for 1 hour to overnight;
4. Place in 1.5 N hydrochloric acid (HCl) for 1 hour under vacuum;
5. Wash with 2 changes with deionized water for 5 minutes each, to remove all of the hydrochloric acid;
6. Dehydrate through 70% ethanol for 30 minutes;
7. Further dehydrate with 100% ethanol for 30 minutes; and
8. Air dry in hood for 1 hour to overnight.

Steps 1-3 are performed to ensure that the scaffold is fully dehydrated prior to the HCl treatment, which in turn ensures that the HCl can uniformly penetrate the scaffold in step 4. Steps 6-8 ensure the implant is fully dehydrated and dried prior to implantation.

Final Implant, Construct or Scaffold

The present invention also includes an implant, scaffold or construct made from this novel method that can be used to treat, replace or repair injury and defect in musculoskeletal tissue, in a subject in need thereof. This implant, construct or scaffold has specific mechanical properties as well as a porous structure to allow the migration and infiltration of cells from tissue adjacent to the implant site, allowing attachment of the implant.

Implantation of the final scaffold is facilitated by fully dehydrating the implant prior to use. The dehydrated implant can be inserted into the musculoskeletal defect in dried form. Upon implantation, it will rehydrate with body fluids and expand to fill the defect of interest. This process can be used to ensure that (1) the scaffold is immediately filled with nutrients and/or cells; and (2) the scaffold has sufficient press-fit with the tissue to ensure that it is held in place.

Specifically, the implant or construct or scaffold would be manufactured by a method comprising the steps of:
1. soaking a sponge made of a biodegradable polymer in deionized water for 1 hour to 5 days and centrifuging the construct during the soaking process to remove trapped air bubbles;
2. substituting the water in the sponge with a non-biodegradable polymer into the sponge under gentle agitation in steps of increasing concentration up to the desired polymer concentration;
3. crosslinking the non-biodegradable polymer; and
4. enzymatically digesting away the biodegradable polymer sponge.

In the preferred embodiment, the construct, implant or scaffold is manufactured by a method comprising the steps of:
1. soaking a gelatin sponge in deionized water for 1 day and centrifuging the construct during the soaking process to remove trapped air bubbles;
2. substituting the water in the sponge with PVA into the sponge under gentle agitation in steps of increasing concentration up to the desired concentration;
3. freezing the construct to −20° C. for 20 hours and then thawing the construct at 25° C. for 4 hours wherein the freeze-thaw process is performed a total of 6 times; and
4. enzymatically digesting away the gelatin sponge.

In a further preferred embodiment, the resulting implant, construct, or scaffold obtained after step (4) would be further digested with hydrochloric acid to digest the non-biodegradable polymer or PVA to increase the pore size. These steps would include:
5. dehydrating the scaffold through 70% ethanol for 30 minutes;
6. further dehydrating with 100% ethanol for 30 minutes;
7. air drying in hood for 1 hour to overnight;
8. placing in 1.5 N hydrochloric acid for 1 hour under vacuum;
9. washing with 2 changes with deionized water for 5 minutes each to remove all of the hydrochloric acid.

In another embodiment, the resulting implant, construct, or scaffold obtained either after step (4) or step (9) is further dehydrated prior to implantation by the following additional steps:
1. dehydrating through 70% ethanol for 30 minutes;
2. further dehydrating with 100% ethanol for 30 minutes; and
3. air drying in hood for 1 hour to overnight.

In a further embodiment, the implant, construct or scaffold made by the methods of the present invention can be attached to another biocompatible composition, either man-made or natural, prior to implantation. Such biocompatible compositions would include, but are not limited to, allografts, osteografts, metal, and bone substitutes.

Mechanical Properties

As stated, the current method can precisely control the mechanical properties of the construct. These mechanical properties measured can include, but are not limited to, the elastic modulus or Young's modulus ($E_Y$), aggregate modulus ($H_A$), Poisson's ratio, and permeability.

Young's modulus is the mathematical description of an object or substance's tendency to be deformed elastically (i.e., non-permanently) when a force is applied to it, and the object is not confined to any direction perpendicular to the force. The elastic modulus of an object is defined as the slope of it stress-strain curve in the elastic deformation region. A stiffer material will have a higher elastic modulus. Young's modulus describes tensile elasticity or the tendency of an object to deform along an axis when opposing forces are applied along that axis; it is defined as the ratio of tensile stress to tensile strain.

When a material is compressed in one direction, it usually tends to expand in the other two directions perpendicular to the direction of compression. This phenomenon is called the Poisson effect. Poisson's ratio (v) is a measure of the Poisson effect. The Poisson ratio is the ratio of the fraction (or percent) of expansion divided by the fraction (or percent) of compression, for small values of these changes.

The equilibrium aggregate modulus ($H_A$) is a measurement of the stiffness of a material when a force is applied to it, the object is confined to prevent expansion in any direction perpendicular to the applied force, and then at equilibrium when fluid has ceased flowing through it. The aggregate modulus can be calculated from Young's modulus and the Poisson ratio.

Hydraulic permeability (k) is a measurement of the ease of water to flow through an object. Permeability can be directly measured as the resistance to flow of fluid through a material using a "direct permeation test" or can be calculated for biphasic material, such as the scaffold, through a mathematical curve fitting of the stress-strain curves obtained testing for $H_A$.

It has been found that increasing the final concentration of the PVA in the implant, construct or scaffold increases the Young's modulus, showing that the greater the concentration of PVA, the stiffer the scaffold. However, it has also been surprisingly found that the permeability of the porous final scaffold was unchanged even when the concentration of PVA was increased, showing the method can modify the mechanical properties of the scaffold, e.g., stiffness, while not affecting the scaffold porosity and permeability which is important to cell integration (Examples 1 and 2; FIG. 1; Table 1). Thus, one embodiment of the present invention is the method for controlling the resulting mechanical properties of the implant by varying the final concentration of the PVA or other non-biodegradable polymer without modifying the porosity and permeability.

As stated above, PVA is physically cross-linked by freeze-thaw cycles. Thus a further embodiment of the present invention is a method of controlling the mechanical properties of the implant by increasing or decreasing the number of freeze-thaw cycles. The mechanical properties can also be controlled by the duration and rate of freezing and thawing during the manufacturing process.

Porosity and Cellular Integration

Another important aspect of the current invention is the implant, construct or scaffold made by the current method must have the ability to be integrated into the tissue. This is achieved by surrounding cells integrating into the scaffold upon implantation into the body. Thus, any implant, construct or scaffold made by the present method must be porous and permeable to allow cells to infiltrate the construct.

A chondrocyte is 10 to 30 μm in diameter. Thus, a construct with a pore size larger than 10 μm would allow for migration and infiltration of these cells. In order for fibrochondrocytes to move into and through a material, pore sizes of around 100 μm are required. The porosity of the final construct is determined by the porosity of the original sponge starting material and can be easily modified by the person of skill in the art in order to obtain optimum porosity. Additionally, the porosity of the final implant can be varied by a controlled digestion with hydrochloric acid (Example 8).

As shown in Example 1 and FIG. 1, a scaffold of the present invention has an average pore diameter of 15.7 µm and apparent porosity of about 81%, irrespective of the final PVA concentration of the scaffold. As shown in Example 8 and FIG. 7, digestion with hydrochloric acid results in a scaffold with an average pore size of about 100-200 µm. By controlling the digestion of the PVA with the HCl, a scaffold of the present invention can be also manufactured with an average pore size of about 30 to 100 µm.

Figure 2:
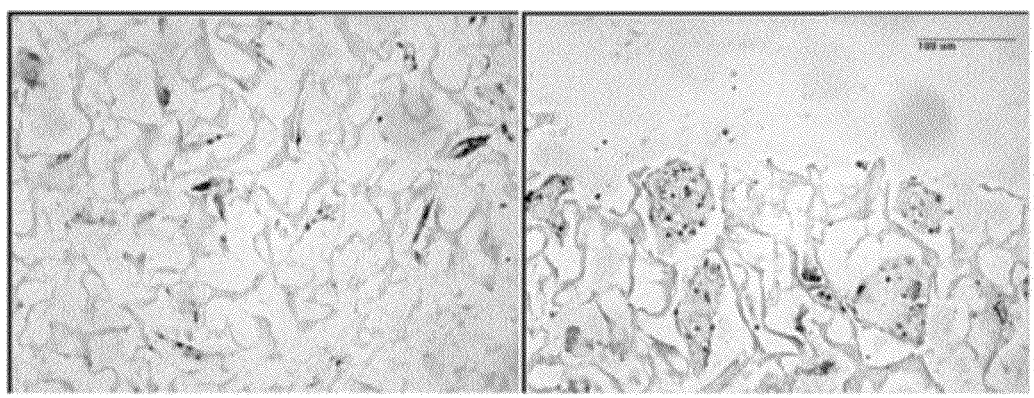
FIG. 2 shows images using immunohistochemistry for assessment of the uptake of bromodeoxyuridine (BrdU). Porous gels manufactured by the method of the present invention that were dynamically loaded were positive for BrdU cells.

More importantly, as shown in Example 3 and FIG. 2, chondrocytes were able to proliferate in a scaffold of the present invention, a finding not previously demonstrated by other research in the field. Additionally, as shown in Example 4 and FIG. 3, chondrocytes migrate into the scaffold of the current invention, again a result not previously shown by other research.

Figure 4:
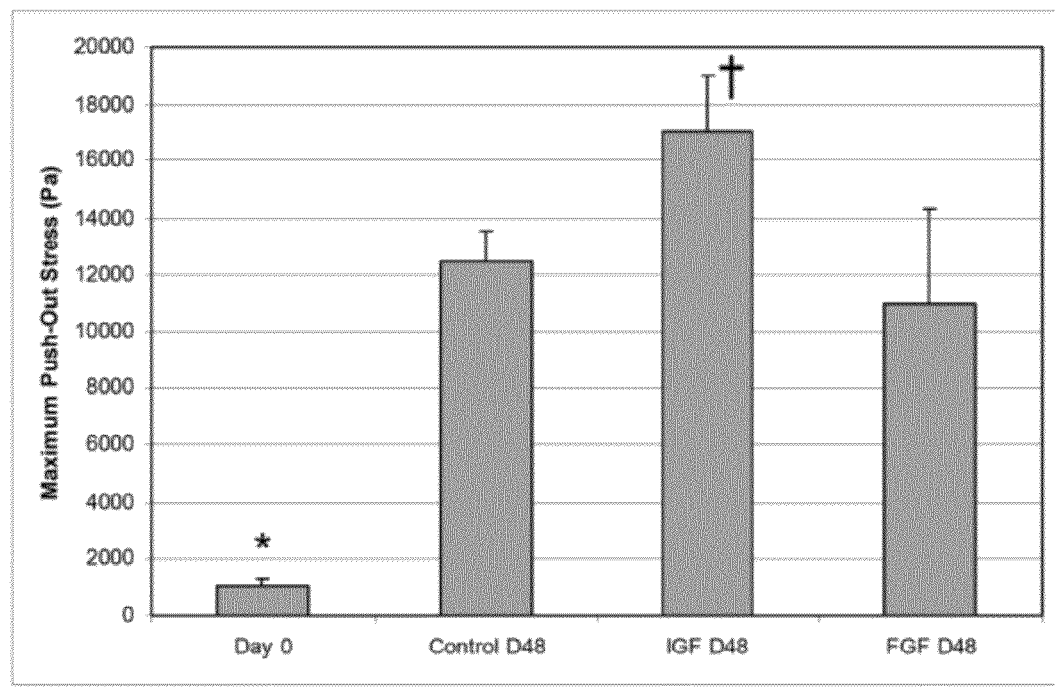
FIG. 4 is a graph depicting the maximum push-out stress endured by scaffolds manufactured by the method of present invention, after migration into the scaffold by chondrocytes.

Even more surprisingly, the strength of the scaffold actually increases with the infiltration of the surrounding cells (Example 5; FIG. 4).

These results show that the implant, construct, or scaffold of the current invention succeeds where other similar implants have failed, in that it can support the migration, growth and proliferation of cells from tissues adjacent to implant site, and thus, insure not only attachment of the scaffold but increased strength.

Two-Zoned Construct

A further embodiment of the present invention is an implant, construct or scaffold wherein the present porosity and pore diameter vary regionally throughout the scaffold. The underlying concept of this embodiment of the present invention is that the mechanical properties of the core of the PVA implant can be tailored to carry load much in the same way of the native tissue, while the periphery of the implant can be optimized to facilitate cell ingress and integration. Use of a non-cell based scaffold which can facilitate mechanical functionality and integration is a significant departure from current paradigms, which hold that fully cell-seeded constructs are the ideal.

By augmenting the porous periphery with a solid internal core, the mechanical properties of the construct can also be tailored to maximize the ability of the scaffold to carry load. The preferred embodiment of this method would result in a construct with a zero porosity in the center of the construct that is able to carry load, and a pre-determined porosity at the periphery of the construct to optimize the ability to integrate into biological tissue.

As shown in Example 6, the construct is manufactured using the method described above through the freeze-thaw cycle. Then a portion of the sponge of a predetermined size, preferably at the center of the sponge, is cored out and filled with a PVA solution. The sponge is then freeze-thawed for additional cycles, and digested with collagenase or another suitable enzyme.

Figure 5:
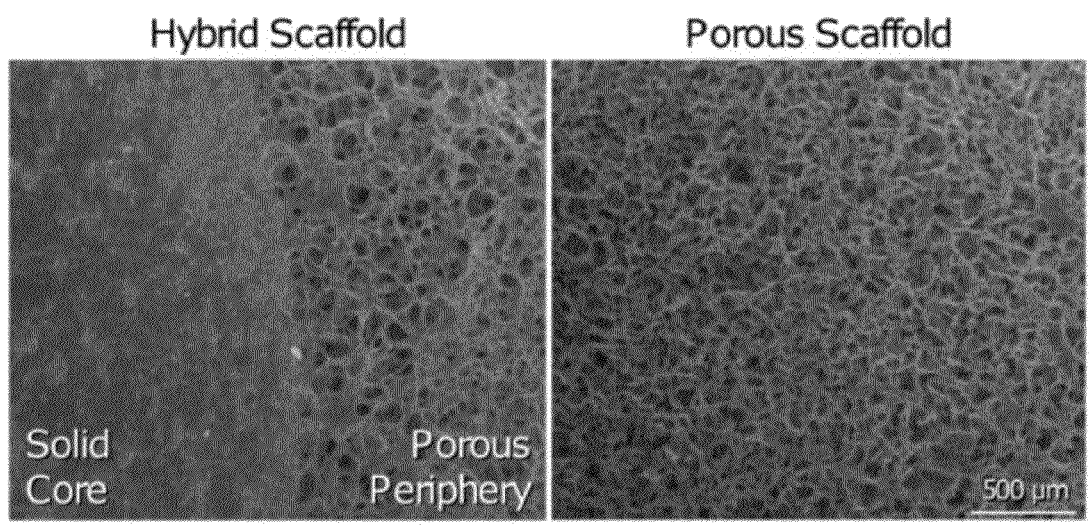
FIG. 5 depicts an ESEM image of a hybrid construct with a solid PVA core and porous periphery (left), and a porous scaffold (right), both manufactured by the method of the present invention.

The resulting construct created contains a solid PVA core and a porous periphery (FIG. 5). The addition of the solid core over doubles the compressive modulus of the implant, construct or scaffold. This hybrid scaffold presents a modular design where the modulus of the polymer core can be controlled and the porous periphery can facilitate cell infiltration towards tissue integration, and represents real progress in a treatment option for repair and replacement of musculoskeletal tissue.

Additionally, the periphery of the two-zoned construct can be further treated as described in Example 7, by dehydrating the periphery with ethanol, and treating with HCl, under controlled conditions, in order to increase the porosity of the periphery. While methods to accomplish this are within the skill in the art, one such method for accomplishing this would be to place the implant on a rotating skewer and rotating it through a bath of HCl.

Tissue Repair and Replacement

The implant, construct or scaffold of the current invention can be used to treat, replace or repair defects and/or injuries in various musculoskeletal tissues, in a subject in need thereof, preferably a mammal, and most preferably a human. Musculoskeletal tissue contemplated to be treated, replaced or repaired includes bone, tendon, ligaments, cartilage and the discs of the spine. In a preferred embodiment the implant is used to stabilize a chrondral defect, which is a defect in the articular cartilage at the end of the bones. In a most preferred embodiment, the chondral defect is found in the knee. The implant would not only repair the defect but protect the surrounding tissue from degradation.

Those of skill in the art would appreciate that the implants, constructs or scaffolds of the present invention may be implanted into a subject using operative techniques and procedures, utilizing such techniques as magnetic resonance imaging and computer guided technology.

EXAMPLES

The present invention may be better understood by reference to the following non-limiting examples, which are presented in order to more fully illustrate the preferred embodiments of the invention. They should in no way be construed to limit the broad scope of the invention.

Example 1

Manufacture of the Interconnected PVA Implant

Materials and Methods

All handling and fabrication techniques were performed aseptically to minimize contamination with bacteria and other infectious agents. The method of manufacture involves four steps:

a. Hydration of gelatin sponges,
b. Replacement of water with poly(vinyl) alcohol solutions,
c. Freeze-thawing of construct, and
d. Removal of gelatin sponge to form macroporous network.

Hydration of Gelatin Sponges:

Gelatin (denatured collagen) sponges (Ethicon-Johnson & Johnson, Somerville, N.J.) were first soaked in deionized water until the entire sponge was saturated with water via capillary action and under applied vacuum (30 minutes on/off for 6 hours) for 1 day. The sponges were transferred to 50 mL conical tubes and repeatedly centrifuged at 3000 g for 1 hour at a time, with gentle agitation of the tube between centrifugations to restore its original shape, until all remaining air bubbles had been removed.

Replacement of Water with Polyvinyl Alcohol Solutions:

Three poly(vinyl) alcohol (PVA) solutions were created: 1%, 5%, and 10% weight/volume solutions. These were prepared by heating 1, 5, or 10 grams of PVA, respectively, in 100 milliliters of deionized water at 121° C. under high pressure. Each solution was stirred and allowed to cool for a few minutes and then the sponges were sequentially soaked and agitated in this series of poly(vinyl) alcohol solutions (1%, 5%, 10%) for 5 days each under gentle agitation/rocking. At the final desired concentration, one additional change of fresh PVA solution was performed prior to freeze-thawing.

Freeze-Thawing:

The PVA-soaked sponges were then placed in 100 mm Petri dishes and frozen to −20° C. for 20 hours and then thawed at 25° C. for 4 hours, with this freeze-thaw process repeated 5 additional times (6 total freeze-thaw cycles).

Removal of Gelatin Sponge to Form Macroporous Network:

The sponges were digested for 24 hours with an enzyme to degrade the collagen sponge (collagenase, Worthington Biochemical Corp., Lakewood, N.J.) at a concentration of 500 enzyme activity units/milliliter. The resulting PVA scaffolds are then cut to size and then soaked in 100% ethanol and allowed to air dry prior to use.

10% and 20% PVA scaffolds (n=6 per group) were evaluated under environmental scanning electron microscopy ("ESEM") that allowed for the samples to be viewed in their hydrated state. Images were taken at 5 different positions along the surface and were then processed in ImageJ (NIH, Bethesda, Md.) to determine pore size and apparent porosity.

Results

Under ESEM, scaffolds had a macroporous, randomly oriented, fibrous appearance with an average pore diameter of 15.7 μm (FIG. 1) with an apparent porosity of 81±3%. No significant differences were noted between the PVA concentrations.

These results demonstrate the ability to modify the natural PVA morphology to possess pores that are large enough to allow for cellular migration, which must be approximately 10 μm diameter.

Example 2

Control of the Mechanical Properties of the Implant for a Given Morphology

Materials and Methods

10% and 20% PVA scaffolds were manufactured using the materials and methods described in Example 1.

Cylindrical scaffolds (Ø5×2-3.5 mm) were cored out for mechanical testing (n=5 per group). Samples were first tested in unconfined compression in a phosphate buffered saline bath. Initial contact with the specimen surface was determined when an instantaneous applied load reading of 0.2-0.5 g was measured and the initial specimen height was determined at this point. Then applied strain (displacement/original height) compressions were applied in 5% increments to a maximum of 25% strain, with the sample being allowed to equilibrate after each step for 10-15 minutes. After each test, the samples were unloaded and allowed to recover to their original height in a saline bath. Samples were then retested in confined compression loading configuration.

The loads were converted to stresses based on construct surface area and the stress/strain information was used to calculate a Young's modulus (from the unconfined tests) and an aggregate modulus (from the confined tests). Poisson's ratio (υ) and permeability (k) were calculated from the compression test data using mathematical models (Jurvelin. et al. (1997); Mow et al. (1980)). Material properties were compared using one-way ANOVA with Fisher LSD post-hoc tests (α=0.05).

Results

Equilibrium aggregate modulus ($H_A$) and elastic modulus ($E_Y$) significantly increased with increasing PVA (Table 1). No differences in v or k were found between PVA concentrations. No strain dependence was found for any of the mechanical parameters measured.

TABLE 1

Macroporous PVA hydrogel material properties.

| | $H_A$ (kPa) | $E_Y$ (kPa) | Y | k ($\times 10^{-11}$ m$^4$/Ns) |
|---|---|---|---|---|
| 10% PVA | 16.2 ± 2.4 | 14.5 ± 2.2 | 0.19 ± 0.05 | 1.88 ± 0.62 |
| 20% PVA | 55.6 ± 2.7* | 48.1 ± 1.2* | 0.22 ± 0.02 | 1.22 ± 0.41 |

*p < 0.05 between gel concentrations.

These findings show that the morphology (from the ESEM in FIG. 1) and the permeability of the porous PVA gel (related to the interconnected pores of the gel) are independent of the gel mechanical properties, which can be modified by changing the gel concentration.

Example 3

Implants can Support Cell Survival and Proliferation

Materials and Methods

PVA scaffolds (Ø5.0×2.5 mm) prepared as described in Example 1 were rehydrated in 400 μL of Dulbecco's Modified Eagle Medium (DMEM) containing 20×10$^6$ chondrocytes/mL in a 24-well plate. After this initial rehydration, scaffolds were covered with an addition 2 mL of cell suspension and incubated at 37° C. with 5% $CO_2$ for 30 minutes. Afterwards, the media was changed with fresh DMEM with 5% fetal bovine serum and antibiotics. After 48 hours, cell-seeded scaffolds were placed in a custom loading bioreactor and loaded in unconfined compression from 0→1 N at 0.5 Hz for 5 minutes at 25° C. Free-swelling (unloaded) controls were maintained adjacent to the bioreactor during loading. After loading, all samples were cultured for an additional 48 hours in DMEM with 10 μM bromodeoxyuridine (BrdU) and then washed for 2 hours in fresh media, fixed in 10% formalin, embedded in paraffin wax, sectioned, and then assessed for BrdU using immunohistochemistry.

Results

All gels were recovered intact after loading. Cells exhibited positive staining for BrdU in both dynamically loaded (DL) and free-swelling (FS) groups with no qualitative differences noted (FIG. 2) which demonstrates the ability of chondrocytes to survive and proliferate within the porous gel, a finding not previously demonstrated by other researchers in the field.

Example 4

Ability of Chrondrocytes to Migrate from Articular Cartilage into the Porous Implant Materials and Methods Cartilage explants (Ø8.5×2.5 mm) were cored out of the trochlear groove and femoral condyles of calves with the superficial and deep zones removed via sharp dissection. Defects (Ø3.5 mm) were created using a sterile biopsy punch and filled with cell-free or cell-seeded (with 20 million chondrocytes/mL, approximately 400 μL per construct). 10% PVA scaffolds made using the procedure of Example 1, were pre-treated with or without 10 U/mL collagenase (Bos et al. (1980); van de Breevaart Bravenboer et al. (2004)) for 15 minutes to create the following groups: cell-free+collagenase, cell-free control, cell-seeded+collagenase, cell-seeded control. Explant-scaffold constructs were cultured for 28 days in DMEM with ITS+, dexamethasone, and ascorbate (fresh daily). Constructs were removed biweekly and fixed in 10% formalin+0.5% cetylpyridinium chloride, cryoprotected in a 30% sucrose solution, embedded in 5% gelatin+5% sucrose embedding medium, and cryotomed for histological analysis of cell infiltration via hematoxylin and Safranin-O histological stains.

Results

Figure 3:
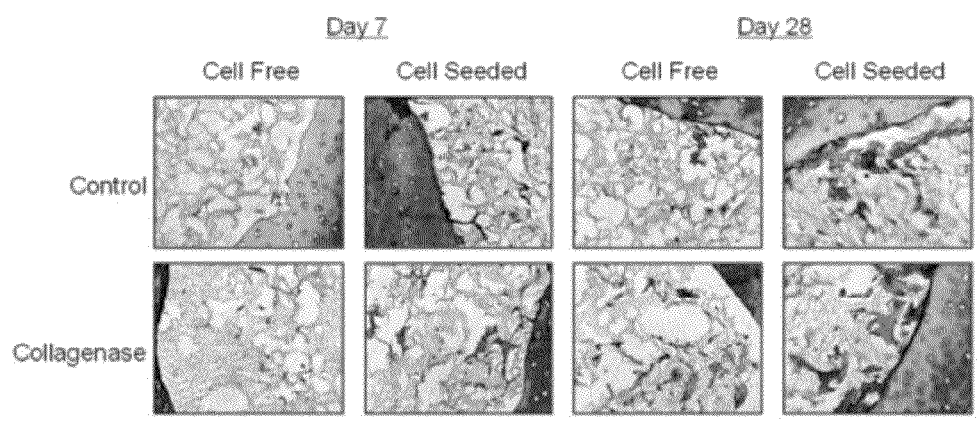
FIG. 3 shows the histological staining of scaffold-cartilage constructs, at Day 7 and Day 28.

Cartilage annuli showed no swelling and no gap formation between the scaffold and cartilage annuli throughout the experimental culture period. On day 7 cell-free control constructs showed some cell migration into approximately the outer 100 μm of the scaffold (FIG. 3). However, cell-free+ collagenase demonstrated some evidence of cell migration into the peripheral at approximately 300 μm of the scaffold (FIG. 3). By day 28, both scaffolds showed increased cell migration into the center of the scaffold, but cell-free+collagenase constructs showed greater cell numbers and deeper migration, with intense Safranin O (red color) matrix staining. Cell-seeded scaffolds acted as positive controls and showed that cells within the constructs are viable over the entire 28 day period (FIG. 3). These results are the first to demonstrate that chondrocytes can migrate into a press-fit, macro-porous scaffold in a cartilage defect model.

Example 5

Ability of Chrondrocytes to Increase the Interfacial

Strength of the Porous Implant-Articular Cartilage Boundary

Materials and Methods

Macroporous PVA scaffolds (Ø5×2.5 mm) made as described in Example 1 were then press-fitted into collagenase-treated cartilage rings (Ø8.5×2.5 mm, Ø3.5 mm hole) as described in Example 4. These explant-scaffold constructs were cultured as described in Example 4 for 48 days with or without supplementation with 100 ng/mL insulin-like growth factor I (IGF-1) or 10 ng/mL fibroblast growth factor-2 (FGF-2). Interfacial strength was assessed on day 0 (before any growth factors were used) and on day 48. The explant-scaffold construct was placed in a custom designed chamber that clamped the cartilage tissue to prevent buckling. Then an indenter was aligned and advanced at 10 μm/s until the scaffold was pushed out of the cartilage ring.

The measured forces were converted into stress values based on measured surface area in contact at the interface.

Results

It was found that the maximum push-out stress increased over time in culture was approximately 2-fold without growth factor supplementation (*p<0.05 vs. all other groups) and approximately 7-fold with IGF-1 supplementation (p<0.05 vs. all other groups) (FIG. 4). FGF-2 was found to have no significant effect on the interfacial strength. These results demonstrate that the interface being formed by the chondrocytes that are migrating into the scaffold increases in strength over time.

Example 6

Manufacture of an Implant where the Percent Porosity Varies Regionally Throughout the Implant, from Zero Porosity in the Center to a Pre-Determined Porosity at the Periphery Materials and Methods Cylindrical gelatin sponges (Ø7×2 mm) were impregnated with 10% polyvinyl-alcohol (PVA) solution and freeze-thawed 6 times as described in Example 1. A Ø5 mm hole was cored out of the sponges and filled 10% PVA solution. All sponges were freeze-thawed an additional 6 times and digested with collagenase. The constructs were imaged using ESEM, as described in Example 1.

Results

The resulting cylindrical construct with a solid PVA core and a porous periphery is evident under ESEM (FIG. 5).

Adding this solid core increased the compressive modulus from approximately 12 kPa for an entirely porous scaffold to approximately 5 kPa for the composite solid-porous scaffold. This hybrid scaffold presents a modular design where the modulus of the polymer core can be controlled and the porous periphery can facilitate cell infiltration towards tissue integration.

These findings show that the porous PVA implant can be modified into a composite form that increases the overall scaffold ability to bear mechanical loads. Each element of the composite scaffold (solid core, porous periphery) can be modified to further accomplish this goal.

Example 7

Ability of the Solid Core to Carry Load as a Function of Modulus

Materials and Methods

Solid cylinders of PVA were manufactured at either 10%, 20% or 40% weight/volume concentration as described in Example 1. The cylinders were tested in unconfined compression with an applied strain of 5% and the modulus values were found to be 20.4±2.5, 164.1±21.7, and 332.7±45.0 kPa, respectively.

Two human cadaveric knees were stripped of soft tissue sparing the capsule, collateral ligaments, cruciate ligaments, and the menisci. Femoral condylar width and length as well as tibial depth, width, and slope were measured for each specimen. All knees were pinned through the epicondylar axis under fluoroscopy and then aligned with the flexion-extension axis of a load-controlled Stanmore Knee Simulator which was programmed to apply dynamic gait loads across the knees as per ISO standard #14243-1. A pressure sensor (4010N, Tekscan Inc., MA) was calibrated and inserted below the medial meniscus, and data were recorded at 9.5 Hz for 20 gait cycles for the ACL intact and transected condition. Peak contact pressure magnitude, peak contact pressure location (as measured by the magnitude of pressure in each of four quadrants in the medial plateau—anterocentral, anteroperipheral, posterocentral, posteroperipheral), knee translation, center of rotation and amount of rotation were computed at 14% and 45% of gait which correspond to the two most pronounced peaks in axial force during gait.

The knees were tested (i) intact (ii) in the presence of a surgically created osteochondral defect (Ø10×10 mm) in the lateral femoral condyle (iii) with a 10% PVA cylinder implanted into the defect site (iv) with a 20% PVA disc implanted into the defect site (v) with a 20% PVA cylinder implanted into the defect site (vi) with a 40% PVA cylinder implanted into the defect site. All implants were press-fit into the defect site and were oversized relative to the defect by 5%.

Results

Figure 6:
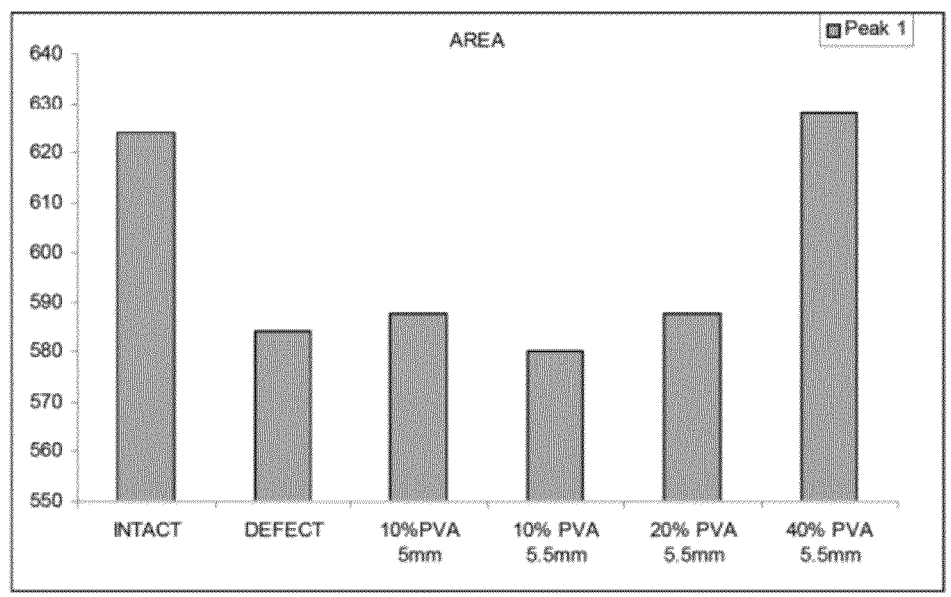
FIG. 6 is a graph showing the results of testing of contact area in intact knees, defective knees, and those implanted with 10%, 20% or 40% PVA cylinders.

Results demonstrated that the contact area of the intact knee was only restored upon implantation of the 40% PVA implant demonstrating that the stiffer construct carried load much in the way of the native tissue (FIG. 6).

Example 8

Increasing Pore Size by Digestion with Hydrochloric Acid

Materials and Methods

Fifteen (15) PVA scaffold were manufactured using the materials and methods of Example 1, were dehydrated in 70% ethanol for 30 minutes, and then further dehydrated with 100% ethanol for 30 minutes, and then subsequently air dried in a hood for 1 hour. Three (3) PVA scaffolds were treated for either 15, 20, 60 or 100 minutes with hydrochloric acid (HCl) at a concentration of 1.5 N. After HCl degradation, the PVA scaffolds were washed twice with double distilled water for 5 minutes each followed by serial dehydration in 70% ethanol and 100% ethanol for 30 minutes each. The ethanol was removed and the scaffolds were air dried in a hood for 1 hour.

The scaffolds were rehydrated for 30 minutes in water before imaging using ESEM, as described in Example 1.

Results

Figure 7:
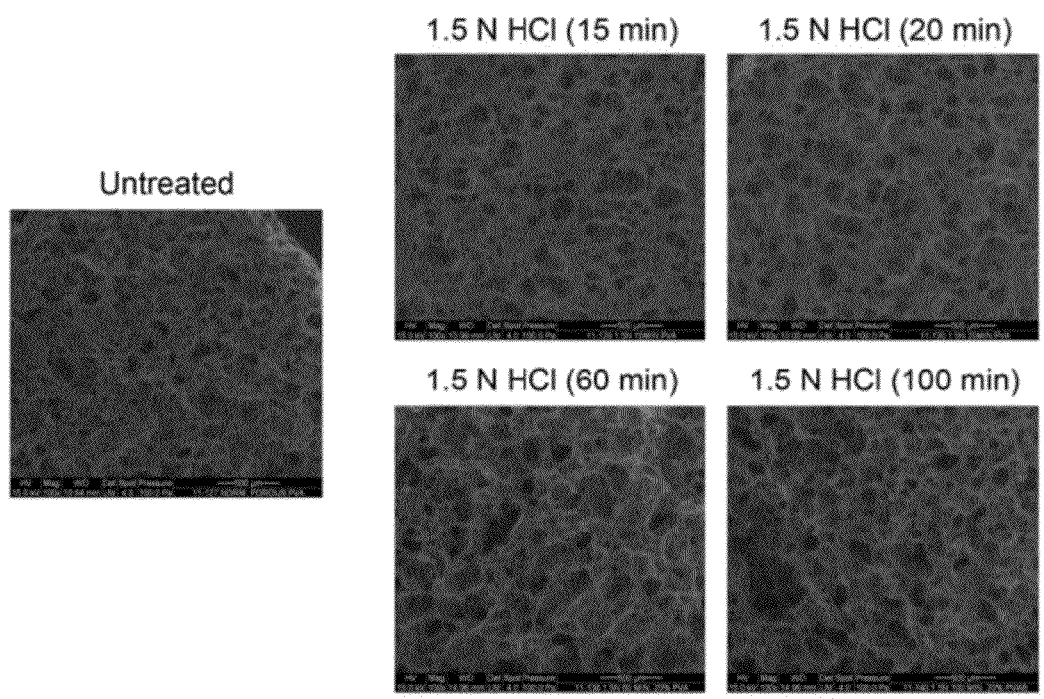
FIG. 7 is series of ESEM images of porous 20% PVA gels showing the effect of 1.5 N hydrochloric acid (HCl) as a function of PVA gel digestion time.

As shown in FIG. 7, at times up to 60 minutes, a progressive increase in pore size is demonstrated with pore sizes ranging from approximately 10 μm in the untreated version, to approximately 100-200 μm with 60 minutes of HCl exposure.

Increasing beyond 60 minutes of incubation time does not result in further increase in porosity, but only results in uncontrolled erosion of the implant.

Example 9

Manufacture of a PVA Scaffold Attached to an Allograft

Materials And Methods

A PVA scaffold manufactured as described in Example 1, was rehydrated with water and then a 50 uL drop of PVA was placed on the surface of the rehydrated porous PVA scaffold and an allograft was placed on top of the porous PVA scaffold. The allograft-porous PVA scaffold was then quickly frozen on dry ice and followed by a series of freeze thaw cycles (about −20° C. for about 20 hours and then thawed at about 25° C. for about 4 hours). The composites were then removed and dehydrated first in 70% ethanol followed by 100% ethanol each for 30 minutes. Samples were then removed from the ethanol and air dried in a hood for 1 hour to overnight.

Results

Figure 8:
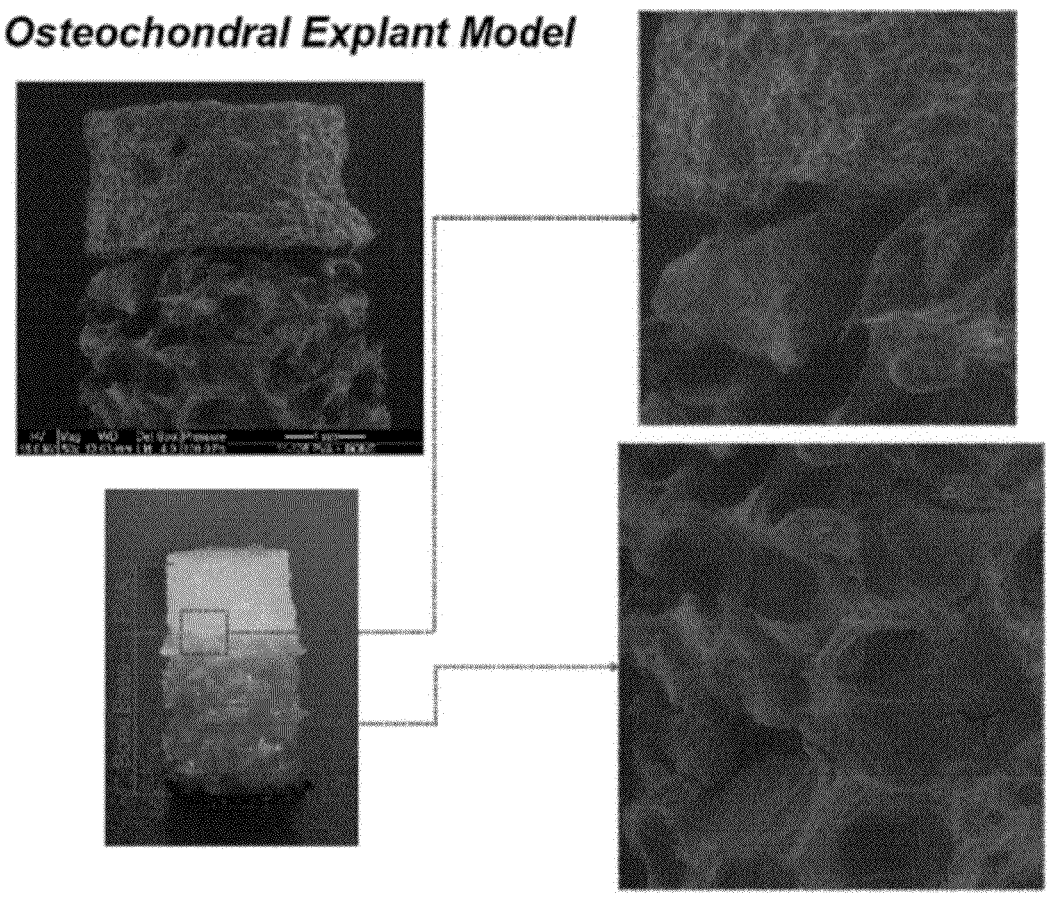
FIG. 8 are images of a PVA implant attached to a bone base.

As seen in FIG. 8, the PVA scaffold attached to the allograft.

REFERENCES

1. Abusafieh et al. (1997) Development of Self-Anchoring Bone Implants. I. Processing and Material Characterization, *J Biomed Mater Res.* 38(4):314
2. Bichara et al. (2010) Porous Poly(vinyl alcohol)-Alginate Gel Hyrid Construct for Neocartilage Formation using Human Nasoseptal Cells, *J. Surg. Res.* 163:331
3. Bos et al. (2002) Specific Enzymatic Treatment of Bovine and Human Articular Cartilage: Implications for Integrative Cartilage Repair, *Arthritis Rheum.* 46(4): 976
4. Bodugoz-Senturk et al. (2009) Poly(vinyl alcohol)-acrylamide Hydrogels as Load-Bearing Cartilage Substitute, *Biomaterials* 30(4):589
5. Bodugoz-Senturk et al. (2008) The Effect of Polyethylene glycol of the Stability of Pores in Polyvinyl Alcohol Hydrogels during Annealing, *Biomaterials* 29(2):141
6. Brittberg et al. (2003) Articular Cartilage Engineering with Autologous Chrondrocyte Transplantation: A Review of Recent Developments, *J. Bone Joint Surg Am* 85(Supp3): 109
7. Buckwalter et al. (1998) Articular Cartilage: Tissue design and Chondrocyte-matrix interactions, *Instr. Course Lect.* 46:477
8. Cho et al. (2005) Fabrication and Characterization of Porous Alginate/Polyvinyl Alcohol Hybrid Scaffolds for 3D Cell Culture, *J. Biomater. Sci. Polm. Ed.* 16(8):933
9. Dai et al. (2002) Gel Impregnated Pore Membrane with Mesh-size Asymetry for Biohybrid Artificial Organs, *Biomaterials* 21(13):1363
10. Freedman et al. (2003) Marrow Stimulation Technique to Augment Meniscus Repair, *Arthroscopy* 19:794
11. Fussell et al. (2005) The Effect of Protein-free versus Protein-containing Medium on the Mechanical Properties and Uptake of Ions of PVA/PVP Hydrogels, *J. Biomater. Sci. Polm. Ed* 16(4):489
12. Gross et al. (2003) Cartilage Resurfacing: Filling Defects, *J. Arthroplasty* 18 (3 Suppl.1):14
13. Jurvelin et al. (1997) Optical and Mechanical Determination of Poisson's ratio of Adult Bovine Humeral Articular Cartilage, *J. Biomech.* 30(3): 235
14. Maher et al. (2007) Nondegradable Hydrogels for the Treatment of Focal Cartilage Defects, *J Biomed Mater Res* 83(A):145
15. Mow et al. (1993) Biomechanics of Diarthrodial Joints: A Review of Twenty Years of Progress, *J. Biomech. Eng.* 115:460
16. Mow et al. (1980) Biphasic Creep and Stress Relaxation of Articular Cartilage in Compression: Theory and Experiments, *J Biomech. Eng,* 102(1): 73
17. Noguchi et al. (1991) Poly(vinyl alcohol) Hydrogel as an Artificial Articular Cartilage: Evaluation of Bio compatibility, *J. Applied Biomater.* 2:101
18. Oka et al. (1990) Development of an Artificial Articular Cartilage, *Clin. Mater.* 6:361
19. Scholten et al. (2010) A Semi-degradable Composite Scaffold for Articular Cartilage Defects, *J. Biomedical Materials Res. A* 97(A):8
20. Stammen et al., (2001) Mechanical Properties of a Novel PVA Hydrogel in Shear and Unconfined Compression, *Biomaterials* 22(8):799
21. Swieszkowski et al. (2006) An Elastic Material for Cartilage Replacement in an Arthritic Shoulder Joint, *Biomaterials* 27(8):1534
22. Szerb et al. (2005) Mosaicplasty: Long-term Follow-up, *Bull Hosp. Jt. Dis.* 56:54
23. Thomas et al. (2004) The Effect of Dehydration History on PVA/PVP Hydrogels for Nucleus Pulposus Replacement, *J. Biomed. Mater. Res. B Appl. Biomater.* 69(2): 135
24. van de Breevaart Bravenboer et al. (2004) Improved Cartilage Integration and Interfacial Strength after Enzymatic Treatment in a Cartilage Transplantation Model, *Arthritis Res. Ther.* 6(5): R469

The invention claimed is:

1. A method of manufacturing an interconnected porous non-biodegradable polymer implant suitable for implantation into a mammal for the treatment, repair or replacement of defects or injury in musculoskeletal tissue, comprising the steps of:
   a. soaking a sponge containing a biodegradable polymer in deionized water for a period of about 1 hour to 5 days;
   b. centrifuging the sponge during the soaking;
   c. substituting the water with a non-biodegradable polymer in steps of increasing concentration up to a desired final concentration;
   d. freezing the sponge to about −20° C. for about 4 to 24 hours and subsequently thawing the sponge at about 25° C. for about 4 to 12 hours, wherein the freeze-thaw process is performed 1 to 8 times; and e. enzymatically digesting away the biodegradable polymer in the sponge, wherein the mechanical properties of the implant can be controlled by varying the concentration of the non-biodegradable polymer and/or varying the duration and number of freeze-thaw cycles and the interconnected porous non-biodegradable polymer implant has sufficient percent porosity and pore diameter to facilitate integration of cells and attachment within the mammal via ingrowth of surrounding tissue.

2. The method of claim 1, wherein the non-biodegradable polymer is poly(vinyl) alcohol (PVA).

3. The method of claim 2, wherein the final concentration of the PVA in the implant is about 10% to 40%.

4. The method of claim 1, wherein the biodegradable polymer is collagen, gelatin, poly(lactic) acid, poly(glycolic) acid or alginate.

5. The method of claim 2, wherein the freezing of the sponge takes place at about −20° C. for about 20 hours and thawing the sponge takes place at about 25° C. for about 4 hours, and the freeze-thaw process is performed 6 times.

6. The method of claim 1, wherein the enzyme used for the enzymatic digestion of the biodegradable polymer is collagenase.

7. The method of claim 1, wherein the mechanical properties of the implant can be further controlled by varying the degree of enzymatic digestion of the biodegradable polymer.

8. The method of claim 1, wherein the mammal is a human.

9. The method of claim 1, comprising the additional step of dehydrating the implant prior to implantation.

10. The method of claim 1, further comprising dehydrating the implant after performing steps a. to d., and placing the implant in hydrochloric acid at a concentration and for a period of time that allows the digestion of the non-biodegradable polymer in order to obtain a determined final pore diameter of the implant.

11. The method of claim 10, wherein the concentration of the hydrochloric acid is about 1.5N and the period of time is about 15 minutes to 60 minutes.

12. The method of claim 10, wherein the final pore diameter of the implant is about 30 to 200 μm.

13. The method of claim 10, comprising the additional step of dehydrating the implant prior to implantation.

14. The method of claim 1, further comprising removing a section from the implant after performing steps a.-d., adding additional non-biodegradable polymer to the section, performing additional freeze-thaw processes, and enzymatically digesting the entire implant, wherein the resulting implant has varying percent porosity and pore diameter throughout the implant, ranging from zero porosity in the center of the implant to a larger porosity at the periphery of the implant.

15. The method of claim 14, wherein the non-biodegradable polymer is PVA.

16. The method of claim 14, comprising the additional step of dehydrating the implant prior to implantation.

17. The method of claim 14, further comprising dehydrating the periphery of the implant, and placing the periphery of the implant in hydrochloric acid at a concentration and for a period of time that allows the digestion of the non-biodegradable polymer in order to obtain a determined final pore diameter of the periphery of the implant.

18. The method of claim 17, wherein the concentration of the hydrochloric acid is about 1.5N and the period of time is about 15 minutes to 60 minutes.

19. The method of claim 17, comprising the additional step of dehydrating the implant prior to implantation.

* * * * *